(12) United States Patent
Wang et al.

(10) Patent No.: US 11,492,588 B2
(45) Date of Patent: Nov. 8, 2022

(54) LACTOCOCCUS LACTIS SUBSP. LACTIS CCFM1018 AND APPLICATION THEREOF IN PREPARATION OF FOOD AND MEDICINE FOR EXCRETING PLASTICIZER

(71) Applicant: Jiangnan University, Wuxi (CN)

(72) Inventors: Gang Wang, Nuxi (CN); Wei Chen, Wuxi (CN); Qian Chen, Wuxi (CN); Jianxin Zhao, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/019,985

(22) Filed: Sep. 14, 2020

(65) Prior Publication Data
US 2020/0407810 A1  Dec. 31, 2020

Related U.S. Application Data

(63) Continuation of application No. PCT/CN2018/079152, filed on Apr. 16, 2018.

(30) Foreign Application Priority Data

Mar. 15, 2018 (CN) .......................... 201810214924.X

(51) Int. Cl.
| | |
|---|---|
| *A61K 35/747* | (2015.01) |
| *A61K 39/09* | (2006.01) |
| *A61K 35/00* | (2006.01) |
| *A23C 9/123* | (2006.01) |
| *A23L 33/135* | (2016.01) |
| *C12N 1/20* | (2006.01) |

(52) U.S. Cl.
CPC .............. *C12N 1/20* (2013.01); *A23C 9/123* (2013.01); *A23L 33/135* (2016.08); *A61K 35/747* (2013.01); *A61K 39/09* (2013.01); *A23Y 2240/41* (2013.01); *A61K 2035/115* (2013.01)

(58) Field of Classification Search
None
See application file for complete search history.

(56) References Cited

U.S. PATENT DOCUMENTS

2012/0209021 A1  8/2012  Kouba et al.

FOREIGN PATENT DOCUMENTS

| CN | 103347395 A | 10/2013 |
|---|---|---|
| CN | 107523514 A | 12/2017 |

OTHER PUBLICATIONS

Glycerin, p. 1, 2022.*
Velly et al. J. Appl. Microbiol. 117: 729-740, 2014.*
Todorov et al. J. Basic Microbiol. 44: 305-316, 2004.*
Sollid K. What is sucrose? pp. 1-5, 2020.*

\* cited by examiner

*Primary Examiner* — Sarvamangala Devi
(74) *Attorney, Agent, or Firm* — IPro, PLLC; Na Xu

(57) ABSTRACT

The disclosure discloses *Lactococcus lactis* subsp. *lactis* CCFM1018 and application thereof in preparation of food and medicine for excreting a plasticizer, and belongs to the technical field of microorganisms. The *Lactococcus lactis* subsp. *lactis* CCFM1018 not only is significantly better than the intestinal resident bacteria *Escherichia coli* and *Enterococcus faecalis* in terms of the effect of promoting the excretion of DEHP and MEHP, but also is better than the commercial strain *Lactobacillus rhamnosus* LGG. Therefore, the *Lactococcus lactis* subsp. *lactis* CCFM1018 of the disclosure can be used as an effective means to prevent and alleviate body damage caused by DEHP and MEHP, and does not have toxic or side effects of drugs. *Lactococcus lactis* subsp. *lactis* CCFM1018 can be used to prepare pharmaceutical compositions and fermented food for alleviating and preventing the toxicity of DEHP and metabolites thereof, and has a very broad application prospect.

8 Claims, 4 Drawing Sheets control　　　　　　　　DEHP　　　　　　　DEHP+CCFM1018

LACTOCOCCUS LACTIS SUBSP. LACTIS CCFM1018 AND APPLICATION THEREOF IN PREPARATION OF FOOD AND MEDICINE FOR EXCRETING PLASTICIZER

TECHNICAL FIELD

The disclosure relates to *Lactococcus lactis* subsp. *lactis* CCFM1018 and application thereof in preparation of food and medicine for excreting a plasticizer, and belongs to the technical field of microorganisms.

BACKGROUND

As a plasticizer, di(2-ethylhexyl) phthalate (hereinafter referred to as DEHP) is added to plastics to increase their flexibility and plasticity. Due to low price, DEHP is widely used in the production of plastic products such as medical instruments and chemical products, and is currently the most widely used plasticizer in China. In these plastic products, DEHP is mainly combined with other molecules in the form of hydrogen bonds and van der Waals force rather than covalent bonds. Therefore, DEHP is very easy to escape during use, and then migrate into the environment and even the human body, causing harm to animals, plants and human health.

Studies have shown that the absorption and distribution period of DEHP in the human body lasts for about 4-8 h, and most of the DEHP can be completely metabolized by the human body within 24 h. Urine is the main route of excretion of DEHP. 24 h after DEHP enters the human body, less than 10% of the DEHP stock solution is directly excreted in urine, and about 67% of the DEHP is converted into five secondary metabolites and excreted in urine. Because DEHP is fat-soluble, a small amount of DEHP is retained in fat or milk. DEHP stored in adipose tissue cannot be completely metabolized for a long time, and has a half-life of 156 h.

The toxic effect of DEHP on the body is mainly exerted by its metabolite mono(2-ethylhexyl) phthalate (MEHP). DEHP and metabolites MEHP thereof accumulated in the body can produce a variety of toxicity, including reproductive toxicity, liver toxicity, embryo toxicity, thyroid toxicity, neurotoxicity, etc. Because DEHP is a peroxisome proliferator, DEHP can break the redox equilibrium in a cell and increase the level of free radicals such as ROS in the cell. In addition, DEHP and metabolites thereof can also affect the expression of antioxidant genes and lead to accumulation of ROS, thus triggering lipid peroxidation, producing lipid peroxides such as malondialdehyde, and causing oxidative damage. At present, the damage of DEHP to the human body is prevented and alleviated mainly through taking some anti-oxidant bioactive substances such as vitamin C, vitamin E, grape seed extract, and flavonoids. However, a large dose is required to alleviate the toxic effects of DEHP by supplementing active substances, and excessive intake of the active substances can also cause side effects in the body. For example, excessive intake of flavonoids can cause secretion disorders in the human body. Moreover, the above method cannot reduce the intake and residue of the plasticizer in the body. Therefore, it is particularly necessary to find a new and safe prevention and treatment method.

In the currently published literature, there is no patent for alleviating the toxicity of the plasticizer through probiotics. According to existing literature reports, the highest adsorption rate of probiotics to DEHP in vitro is only 9.62%, and the adsorption effect is not ideal. Therefore, it is particularly important to develop a probiotic with strong adsorption capacity for the plasticizer, and prove through animal experiments that the probiotic has a good effect on alleviating the toxic damage of the plasticizer in the body.

SUMMARY

The disclosure provides *Lactococcus lactis* subsp. *lactis* CCFM1018, deposited on Feb. 11, 2018 at the Guangdong Microbial Culture Collection Center, Guangdong Institute of Microbiology, 5$^{th}$ Floor, Building 59, No. 100, Xianlie Middle Road, Guangzhou, with an preservation number of GDMCC No. 60332.

The disclosure further provides a microbial preparation, containing the *Lactococcus lactis* subsp. *lactis* CCFM1018.

In one embodiment, the microbial preparation is a culture solution prepared by fermentation of the *Lactococcus lactis* subsp. *lactis* CCFM1018 in an MRS medium.

In one embodiment, after the *Lactococcus lactis* subsp. *lactis* CCFM1018 is fermented in the MRS medium, bacterial cells are collected and mixed with a cytoprotective agent, and then the mixture is subjected to freeze-drying treatment to obtain a freeze-dried preparation containing live cells of the *Lactococcus lactis* subsp. *lactis* CCFM1018.

In one embodiment, the microbial preparation is a bacterial suspension of the *Lactococcus lactis* subsp. *lactis* CCFM1018.

The disclosure further provides application of *Lactococcus lactis* subsp. *lactis* CCFM1018 in preparation of products capable of promoting excretion of a plasticizer and metabolites thereof from mammals.

The disclosure further provides a method for excreting a plasticizer and metabolites thereof from the body, including taking the food or medicine containing the *Lactococcus lactis* subsp. *lactis* CCFM1018 into the body to achieve the effect of excreting the plasticizer and the metabolites thereof from the body.

In one embodiment, the plasticizer includes di(2-ethylhexyl) phthalate and mono(2-ethylhexyl) phthalate.

In one embodiment, the disclosure further provides application of *Lactococcus lactis* subsp. *lactis* CCFM1018 in preparing probiotics colonized in vivo.

In one embodiment, the *Lactococcus lactis* subsp. *lactis* CCFM1018 can be resistant to gastric acid and bile salts, promote excretion of a plasticizer and metabolites thereof from the body, reduce the content of the plasticizer and the metabolites thereof in serum, and significantly reduce the damage of the plasticizer and the metabolites thereof to testicular tissue and liver tissue.

In one embodiment, the fermented food can be resistant to gastric acid and bile salts, promote excretion of a plasticizer and metabolites thereof from the body, reduce the content of the plasticizer and the metabolites thereof in serum, and significantly reduce the damage of the plasticizer and the metabolites thereof to testicular tissue and liver tissue.

The disclosure further provides a method for preparing a fermented product, including adding the *Lactococcus lactis* subsp. *lactis* CCFM1018 to fermentation raw materials to ferment for a certain period of time to obtain the fermented product.

In one embodiment, the fermented product is food.

In one embodiment, the fermented product is a fermented beverage.

In one embodiment, the fermented food includes dairy products, bean products, and fruit and vegetable products; the dairy products include milk, sour cream, and cheese; and the fruit and vegetable products include cucumber, carrot, beet, celery, and cabbage products.

In one embodiment, the fermented beverage is a fermented dairy product, prepared by inoculating milk with the *Lactococcus lactis* subsp. *lactis* CCFM1018 and fermenting the milk at 30-37° C. for at least 4 h.

The disclosure has the beneficial effects as follows: The *Lactococcus lactis* subsp. *lactis* CCFM1018 of the disclosure has good resistance to gastric acid and bile salts, can promote excretion of the plasticizer DEHP and the metabolite MEHP thereof from the body, reduces the content of the plasticizer and the metabolite thereof in serum, and significantly reduces the damage of the plasticizer and the metabolite thereof to testicular tissue and liver tissue.

The *Lactococcus lactis* subsp. *lactis* CCFM1018 not only is significantly better than the intestinal resident bacteria *Escherichia coli* (DEHP: 5.86%, MEHP: 0.28%) and *Enterococcus faecalis* (DEHP: 1.75%, MEHP: 0.17%) in terms of in vitro adsorption of DEHP and MEHP (57.67% and 67.36% respectively), but also is better than the commercial strain *Lactobacillus rhamnosus* LGG (DEHP: 13.75%, MEHP: 15.60%). In rats, the *Lactococcus lactis* subsp. *lactis* CCFM1018 can significantly reduce the DEHP and MEHP content in serum (by 30.47% and 63.63% respectively compared to the blank control group), and at the same time increase the DEHP and MEHP content in feces (by 58.90% and 21.42% respectively compared to the blank control group). Therefore, the *Lactococcus lactis* subsp. *lactis* CCFM1018 of the disclosure can be used as an effective means to prevent and alleviate body damage caused by DEHP and MEHP, and does not have toxic or side effects of drugs. *Lactococcus lactis* subsp. *lactis* CCFM1018 can be used to prepare pharmaceutical compositions and fermented food for alleviating and preventing the toxicity of DEHP and metabolites thereof, and has a very broad application prospect.

Deposit of Biological Materials

*Lactococcus lactis* subsp. *lactis* CCFM1018 was deposited on Feb. 11, 2018 at the Guangdong Microbial Culture Collection Center, Guangdong Institute of Microbiology, the address is $5^{th}$ Floor, Building 59, No. 100, Xianlie Middle Road, Guangzhou, and the preservation number is GDMCC No. 60332.

DETAILED DESCRIPTION

Figure 1:
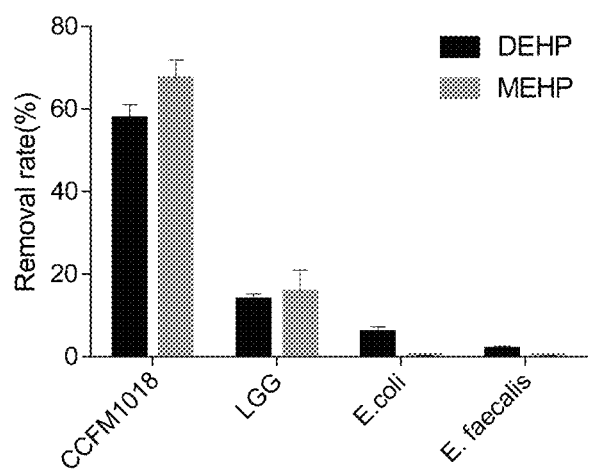
FIG. 1 is a schematic diagram showing comparison in the adsorption capacity of DEHP and MEHP in vitro by the strain of the present application and control strains *Lactobacillus rhamnosus* GG (LGG), *Escherichia coli* and *Enterococcus faecalis*.

*Lactococcus lactis* subsp. *lactis* CCFM1018 of the disclosure was deposited on Feb. 11, 2018 at the Guangdong Microbial Culture Collection Center, Guangdong Institute of Microbiology, the address is $5^{th}$ Floor, Building 59, No. 100, Xianlie Middle Road, Guangzhou, and the preservation number is GDMCC No. 60332.

The *Lactococcus lactis* Subsp. *Lactis* CCFM1018 has the Following Biological Characteristics:

(1) Bacterial characteristics: The bacterium is gram-positive, non-spore forming and non-moving, has oval bacterial cells, and appears in pairs and clusters.

(2) Colony characteristics: Obvious colonies are formed on a culture medium after 36 h of cultivation. The colonies are small, round on the front and protruding on the side, have neat edges, are milky white and opaque, are moist and smooth on the surface, and produce no pigment.

(3) Growth characteristics: The bacterium is a facultative anaerobic bacterium, the optimum growth temperature is 30° C., the growth is good at 32-38° C., and the growth is slow at 45° C. or above. The optimum initial pH is 6-7. The bacterium grows well in a culture solution containing glucose.

(4) The bacterium has good tolerance to artificial simulated gastrointestinal fluid.

(5) The bacterium can alleviate the damage of DEHP and the metabolite MEHP to the testis.

(6) The bacterium can significantly increase the excretion of DEHP and MEHP in feces.

(7) The bacterium can significantly reduce the levels of DEHP and MEHP in serum, and reduce the accumulation of DEHP and MEHP in the body.

(8) The bacterium can significantly improve the activity of superoxide dismutase (SOD) in the liver.

Extraction Method of the Strain:

(I) Isolation and Screening of Lactic Acid Bacteria, Including the Following Steps:

(1) collecting a plurality of fermented vegetable samples, and enriching the samples in GM17 culture media containing sorbitol at 30° C. for 12 h;

(2) carrying out gradient dilution on the enriched samples, spreading the diluted samples on GM17 solid plates supplemented with 0.02% bromcresol purple, and performing culturing for 24-48 h;

(3) selecting individual colonies with obvious color-changing zones and conforming to the basic morphology of lactic acid bacteria, performing plate streaking purification, and screening and isolating lactic acid bacteria; and (4) culturing the above individual colonies in liquid GM17 culture solutions for 24 h, then performing gram staining, and selecting gram-positive bacteria for performing subsequent experiments.

(II) Preliminary Identification of *Lactococcus lactis*: Calcium-Dissolving Zone Determination Method, Including the Following Steps:

(1) culturing the lactic acid bacteria screened in step (I) in a liquid sorbitol GM17 culture solution for culturing the lactic acid bacteria for 24 h, then taking 1 mL of the culture and centrifuging the culture at 8,000×g for 2 min;

(2) washing bacterial cells twice with a 0.05 M $KH_2PO_4$ solution;

(3) resuspending the obtained bacterial paste, streaking the bacterial paste on a sorbitol GM17-0.75% $CaCO_3$ solid culture medium, and culturing the bacteria for 24 h; and (4) selecting colonies with obvious calcium-dissolving zones and being convex, round, fine and white without mycelia, and after gram staining, preliminarily judging the bacteria as *Lactococcus* if the bacterial cells are spherical by microscopic observation.

(III) Molecular Biological Identification of *Lactococcus lactis* Subsp. *Lactis*, Including the Following Steps:

(1) Performing Extraction of a Genome of a Single Bacterium:

A. culturing the lactic acid bacteria screened in step (II) overnight, taking 1 mL of the bacterial suspension cultured overnight in a 1.5 mL centrifuge tube, centrifuging the bacterial suspension at 8,000×g for 2 min, and discarding the supernatant to obtain the bacterial cells;

B. after purging the bacterial cells with 1 mL of sterile water, centrifuging the bacterial cells at 8,000×g for 2 min, and discarding the supernatant to obtain the bacterial cells;

C. adding 200 μL of SDS lysate and placing the mixed solution in a water bath at 80° C. for 30 min;

D. adding 200 μL of phenol-chloroform solution to the bacterial cell lysate, wherein the compositions in volume ratio of the phenol-chloroform solution are Tris saturated phenol:chloroform:isoamyl alcohol=25:24:1; after mixing by inversion, performing centrifuging at 12,000×g for 5-10 min, and taking 200 μL of supernatant;

E. adding 400 μL of absolute alcohol or absolute isopropanol to the 200 μL of supernatant, allowing the mixed solution to stand for 1 h at −20° C., performing centrifuging at 12,000×g for 5-10 min, and discarding the supernatant;

F. adding 500 μL of 70% (volume percentage) absolute alcohol to resuspend the precipitate, performing centrifuging at 12,000×g for 1-3 min, and discarding the supernatant;

G. drying the precipitate in an oven at 60° C., or drying the precipitate naturally; and H. re-dissolving the precipitate with 50 μL of ddH$_2$O for PCR;

(2) Performing 16S rDNA PCR:

A. bacterial 16S rDNA 50 μL PCR reaction system:
10×Taq buffer, 5 μL; dNTP, 5 μL; 27 F, 0.5 μL; 1492R, 0.5 μL; Taq enzyme, 0.5 μL; template, 0.5 μL; ddH$_2$O, 38 μL.

B. PCR Conditions:
95° C. 5 min; 95° C. 10 s; 55° C. 30 s; 72° C. 30 s; step 2-4 30×; 72° C. 5 min; 12° C. 2 min;

(3) preparing a 1% agarose gel, then mixing the PCR product with 10× loading buffer, performing loading at an amount of 5 μL, performing running at 120 V for 30 min, and then performing gel imaging; and (4) performing sequencing analysis on the PCR product of 16S rDNA, using BLAST to search and compare the similarity in GeneBank with the sequence results, selecting a new *Lactobacillus* strain with the sequencing result identified as belonging to *Lactococcus lactis* subsp. *lactis*, and storing the new *Lactobacillus* strain at −80° C. for later use.

Example 1: Tolerance of *Lactococcus lactis* Subsp. *Lactis* CCFM1018 to Simulated Gastrointestinal Fluid A solid culture medium was inoculated with cryopreserved *Lactococcus lactis* subsp. *lactis* CCFM1018 by streaking, and culturing was performed statically and aerobically for 24 h at a temperature of 30° C. After subculturing 2-3 times in a liquid culture solution, the *Lactococcus lactis* subsp. *lactis* CCFM1018 culture solution was taken and centrifuged at 8,000×g for 5 min, and bacterial cells were collected. According to the ratio of 1:1 (m/v), the bacterial cells were resuspended in artificial simulated gastric juice with the pH of 2.5 (an MRS culture medium containing 1% pepsin, pH=2.5), and the solution was mixed and then aerobically cultured at 37° C. Samples were taken at the beginning (0 h), 1 h, 2 h and 3 h respectively. Plate colony counting was performed by pouring culture using an MRS agar culture medium, the number of viable bacteria was determined, and the survival rate was calculated. The survival rate is the ratio of the number of viable bacteria in the culture solution to the number of viable bacteria at 0 h, expressed in %.

The *Lactococcus lactis* subsp. *lactis* CCFM1018 culture solution was taken and centrifuged at 8,000×g for 5 min, and bacterial cells were collected. The bacterial cells (1:1) were resuspended in artificial simulated intestinal juice (an MRS culture medium containing 0.3% bovine bile salt and 1% trypsin, pH=8.0), and then aerobically cultured at 37° C. Samples were taken at the beginning (0 h), 1 h, 2 h, 3 h and 4 h respectively. Plate colony counting was performed by pouring culture using an MRS agar culture medium, the number of viable bacteria was determined, and the survival rate was calculated. The survival rate is the ratio of the number of viable bacteria during sampling in the culture solution to the number of viable bacteria at 0 h, expressed in %. The experimental results are shown in Table 1 and Table 2. It can be seen that *Lactococcus lactis* subsp. *lactis* CCFM1018 has good tolerance to artificial gastric juice and intestinal juice.

TABLE 1

Tolerance of *Lactococcus lactis* subsp, *lactis* CCFM1018 in artificial simulated gastric juice

| | Artificial simulated gastric juice | | |
| --- | --- | --- | --- |
| Treatment time (h) | 1 | 2 | 3 |
| Survival rate (%) | 93.27 ± 2.04 | 90.88 ± 3.25 | 85.39 ± 4.14 |

TABLE 2

Tolerance of *Lactococcus lactis* subsp, *lactis* CCFM1018 in artificial simulated intestinal juice

| | Artificial simulated intestinal juice | | | |
| --- | --- | --- | --- | --- |
| Treatment time (h) | 1 | 2 | 3 | 4 |
| Survival rate (%) | 89.65 ± 6.29 | 82.55 ± 5.58 | 70.32 ± 5.57 | 60.67 ± 6.36 |

Example 2: *Lactococcus lactis* Subsp. *Lactis* CCFM1018 has Good Adsorption Capacity for DEHP and MEHP in an Aqueous Solution Containing Plasticizer DEHP or MEHP In Vitro Adsorption of bacterial cells: After purification and activation culture of experimental bacteria, MRS liquid culture media were inoculated with the bacteria according to an inoculum concentration of 1% (v/v), and culturing was performed at 30° C. for 20 h (*E. coli* was cultured in an LB culture medium at 37° C. with shaking; *E. faecalis* was cultured at 37° C. in an MRS liquid culture medium). Then the culture solutions were centrifuged at 8,000×g for 20 min, and the supernatants were discarded. After resuspension with ultrapure water, centrifugation was performed at 8,000×g for 20 min, and the supernatants were discarded to obtain viable bacterial cells, namely wet bacterial cells. The wet bacterial cells were resuspended in a 50 mg/L DEHP or 10 mg/L MEHP aqueous solution, and the final bacterial cell concentration reached 1 g wet bacterial cells/L. As a blank control, wet bacterial cells were resuspended in ultrapure water without DEHP and MEHP. The volume of each group is 1 mL. The mixed solutions were incubated with shaking at 37° C. for 4 h, and then centrifugation was performed at 3,500×g for 10 min. After the supernatants were collected and passed through a 0.22 μm filter membrane, the content of DEHP or MEHP in the filtrate was determined by UPLC-MS, and the average value was taken for 3 parallel experiments.

Determination of DEHP and MEHP adsorption capacity: The content of remaining DEHP or MEHP in filtrates was determined by UPLC-MS of a Waters EYNAPT MS system, a C18 column (2.1×100 mm, 1.7 μm, Waters Co.) was used, the column temperature was 30° C., and the injection volume was 1 μL. Eluents A and B were 100% methanol and 0.1% (v/v) formic acid aqueous solution respectively, gradient elution was adopted, and the flow rate was 0.3 mL/min. The gradient elution conditions are shown in Table 3.

TABLE 3

| Gradient elution conditions | | | | |
| --- | --- | --- | --- | --- |
| t/min | 0-0.5 | 0.5-7.0 | 7.0-7.5 | 7.5-10.0 |
| Proportion of eluent A | 60% | 60-100% | 100-60% | 60% |

Mass spectrometry conditions: The ionization source was an ESI source; MRM detection (DEHP: MS+; MEHP: MS−) was used; the Capillary was 3.0 KV; the Conc was 40.00 V; the source temperature (radiation source temperature) was 120° C.; the desolvation temperature was 400° C.; the Conc gas flow was 50 L/h; and the desolvation gas flow was 700 L/h. The gas flow rate was 0.1 mL/min; the mass-to-charge ratio scanning range was 100-2,000; the scanning time was 1 s, and the interval was 0.061 s. The results were analyzed by MassLynx V4.1 (Waters Co.). In the study, the minimum detection limits of DEHP and MEHP were 0.05 ppm and 0.1 ppm, respectively. The adsorption rate of lactic acid bacteria was calculated based on the difference in the DEHP or MEHP concentration before and after adsorption, and the adsorption rate was calculated by the following formula:

Adsorption rate (%)=[(The content of plasticizer in an aqueous solution before adsorption−the content of plasticizer in ultrapure water)−(The content of plasticizer in a supernatant after adsorption−the content of plasticizer in a supernatant in the blank control)]/(The content of plasticizer in an aqueous solution before adsorption−the content of plasticizer in ultrapure water)×100.

The determination results are shown in FIG. 1. It is obvious from FIG. 1 that compared with a commercial bacterium LGG (DEHP: 13.75%, MEHP: 15.60%) and intestinal resident bacteria *E. coli* (DEHP: 5.86%, MEHP: 0.28%) and *E. faecalis* (DEHP: 1.75%, MEHP: 0.17%), the adsorption rates (DEHP: 57.67%, MEHP: 67.36%) of the strain *Lactococcus lactis* subsp. *lactis* CCFM1018 of the disclosure are significantly higher than those of the control bacteria, and far higher than the previously reported adsorption rate of 9.62% for DEHP. Therefore, the *Lactococcus lactis* subsp. *lactis* CCFM1018 has good adsorption capacity for DEHP and MEHP.

Example 3: *Lactococcus lactis* Subsp. *Lactis* CCFM1018 has No Acute Toxic or Side Effects on SD Rats

*Lactococcus lactis* subsp. *lactis* CCFM1018 was resuspended in a 2% (w/v) sucrose solution with a bacterial cell density of $1.0 \times 10^9$ CFU/mL. 10 healthy male SD rats weighing about 100 g were taken, given 2 mL of suspension of the above concentration through gavage daily, observed for a week, and recorded for the death and body weight.

The experimental results are listed in Table 4. The results showed that feeding *Lactococcus lactis* subsp. *lactis* CCFM1018 with a concentration of $1.0 \times 10^9$ CFU/mL did not cause significant effects on the rats, and the rats had no significant change in the body weight or death. The rat had no obvious pathological symptoms.

TABLE 4

| Changes in body weight and death of rats | | | | | | | |
| --- | --- | --- | --- | --- | --- | --- | --- |
| Time (d) | 1 | 2 | 3 | 4 | 5 | 6 | 7 |
| Body weight (g) | 100.213 ± 3.85 | 108.547 ± 3.63 | 117.149 ± 5.32 | 128.023 ± 3.72 | 137.643 ± 4.92 | 146.07 ± 6.64 | 159.68 ± 4.41 |
| Death | — | — | — | — | — | — | — |

Note:
— represents no rats died.

Figure 2:
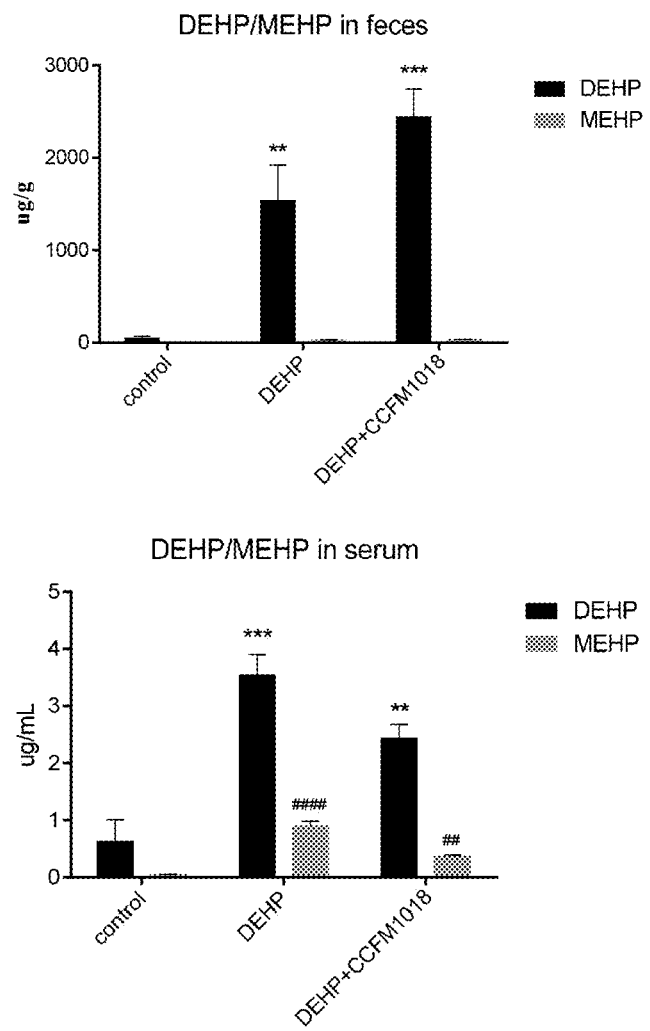
FIG. 2 is a schematic diagram of influence of the strain of the present application on the DEHP and MEHP content in serum and feces.

Example 4: Influence of *Lactococcus lactis* Subsp. *Lactis* CCFM1018 on the DEHP and MEHP Content in Serum and Feces of DEHP-Exposed Rats 18 healthy male SD rats weighing about 100 g were randomly divided into 3 groups: a blank control group (control), a DEHP-exposed model group (DEHP), and a *Lactococcus lactis* subsp. *lactis* CCFM1018 intervention group (DEHP+CCFM1018), and each group contains 6 rats. On days 1-7 of the experiment, the blank control group and the DEHP-exposed model group were given 2 mL of 2% (w/v) sucrose solution through gavage daily, and the rats in the *Lactococcus lactis* subsp. *lactis* CCFM1018 intervention group were given 2 mL of the *Lactococcus lactis* subsp. *lactis* CCFM1018 suspension with a concentration of $1.0 \times 10^9$ CFU/mL prepared according to Example 3 of this specification through gavage. On day 8, the drinking water of the blank control group was changed to an aqueous solution containing 0.05% (m/V) sucrose fatty acid ester. DEHP was dissolved in the 0.05% (m/V) sucrose fatty acid ester aqueous solution, and except the blank group, exposure was performed via the drinking water at a dose of 3,000 mg/kg body weight every day. Gavage with the probiotic and the control 2% (w/v) sucrose solution continued during the exposure period. After four weeks of continuous exposure, the feces were collected and the animals were euthanized. Testes, liver and serum were collected, and the DEHP and MEHP content in the serum and feces were determined. The results of the determination are shown in FIG. 2. In FIG. 2, * indicates significance compared to the DEHP content in the control group; *P<0.05, P<0.01, *P<0.005, ****P<0.001; #P<0.05, ##P<0.01, ###P<0.005, ####P<0.001.

Experimental results showed that after intervention of the *Lactococcus lactis* subsp. *lactis* CCFM1018, the DEHP and MEHP content in serum was significantly reduced (by 30.47% and 63.63% respectively compared to the blank control group), and at the same time the DEHP and MEHP content in feces was increased (by 58.90% and 21.42% respectively compared to the blank control group). This shows that the *Lactococcus lactis* subsp. *lactis* CCFM1018 can effectively promote the excretion of DEHP and the metabolite MEHP from the body.

Figure 3:
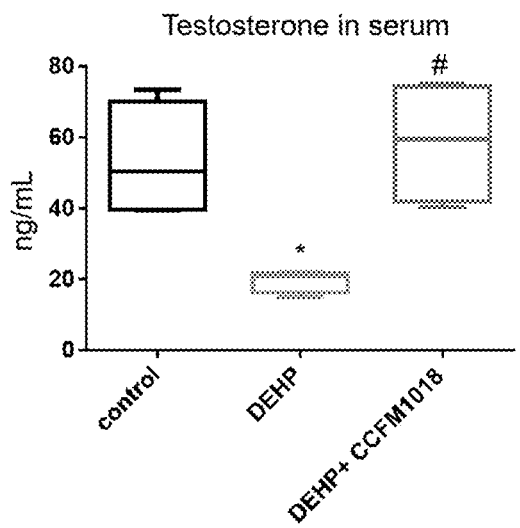
FIG. 3 is a schematic diagram of improvement of the strain of the present application on the level of testosterone in the serum of a DEHP-exposed model rat.

Example 5: Alleviating Effect of *Lactococcus lactis* Subsp. *Lactis* CCFM1018 on the Reproductive Toxicity of DEHP-Exposed Rats The serum obtained in Example 4 was taken, and the testosterone content in the serum was determined according to the method shown in the ELISA kit. The results are shown in FIG. 3. In FIG. 3, * indicates significance compared to the control group, and # indicates significance compared to the model group; *P<0.05, #P<0.05.

Figure 4:
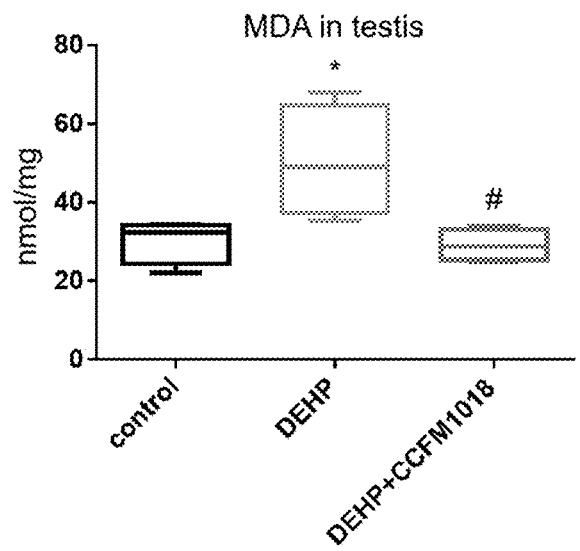
FIG. 4 is a schematic diagram of influence of the strain of the present application on the content of malondialdehyde (MDA) in the testis of a DEHP-exposed model rat.

The testicular tissue obtained in Example 4 was weighed, normal saline was added at a ratio of 1:9 (m/m), and the testicular tissue was broken in a tissue homogenizer to obtain 10% testicular tissue homogenate. The level of malonaldehyde (MDA) in the homogenate was determined. The determination results are shown in FIG. 4. In FIG. 4, * indicates significance compared to the control group, and # indicates significance compared to the DEHP model group; *P<0.05, #P<0.05.

Figure 5:
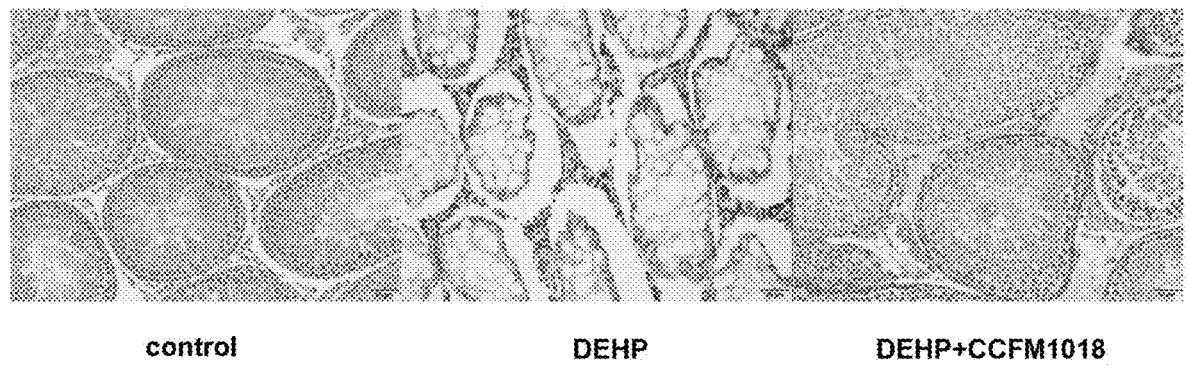
FIG. 5 is a schematic diagram of improvement of the strain of the present application on tissue damage of the testis of a DEHP-exposed model rat.

Testicular tissue was taken for performing paraffin sectioning, and conventional H&E staining was performed. The staining results are shown in FIG. 5.

By comparing the testosterone content in serum, the MDA level in the testis and the testicular pathological indexes of the DEHP-exposed model group and the *Lactococcus lactis* subsp. *lactis* CCFM1018 intervention group, it was found that *Lactococcus lactis* subsp. *lactis* CCFM1018 of the disclosure can alleviate the abnormality in testosterone content in rat serum caused by DEHP intake (DEHP-exposed model group: 19.65 mmol/L, CCFM1018 intervention group: 64.75 mmol/L), reduce the MDA content in the testicular tissue (DEHP-exposed model group: 50.28 nmol/mg, CCFM1018 intervention group: 28.66 nmol/mg), alleviate testicular tissue damage, and play a significant role in alleviating the reproductive damage caused by DEHP intake.

Figure 6:
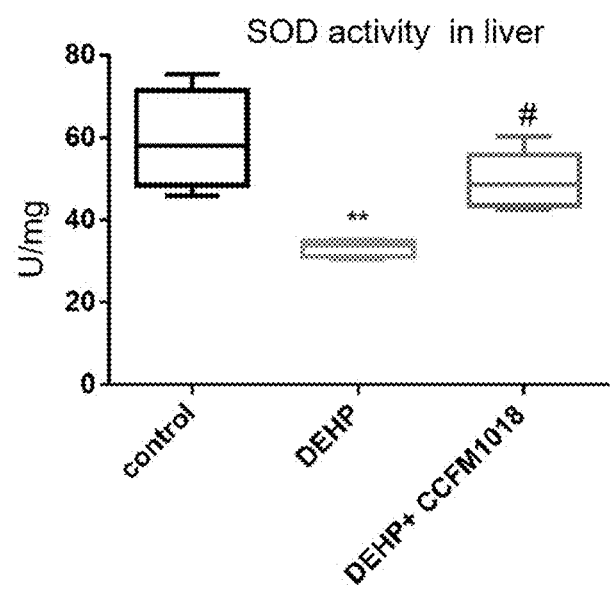
FIG. 6 is a schematic diagram of influence of the strain of the present application on SOD activity in the liver of a DEHP-exposed model rat.

Example 6: *Lactococcus lactis* Subsp. *Lactis* CCFM1018 Improves SOD Activity in the Liver of DEHP-Exposed Rats The liver tissue obtained in Example 4 was weighed, normal saline was added at a ratio of 1:9 (m/m), and the liver tissue was broken in a tissue homogenizer to obtain 10% liver tissue homogenate. The activity level of superoxide dismutase (SOD) in the homogenate was determined. The determination results are shown in FIG. 6. In FIG. 6, * indicates significance compared to the control group, and # indicates significance compared to the DEHP model group; *P<0.05, **P<0.01, #P<0.05. By comparing the SOD activity in the liver of the DEHP-exposed model group and the *Lactococcus lactis* subsp. *lactis* CCFM1018 intervention group (33.29 U/mg and 49.43 U/mg, respectively), it is found that the *Lactococcus lactis* subsp. *lactis* CCFM1018 of the disclosure can effectively improve the SOD activity in liver decreased by the intake of DEHP.

Example 7 Preparation of *Lactococcus lactis* Subsp. *Lactis* CCFM1018 Fermentation Agent An MRS culture medium was inoculated with *Lactococcus lactis* subsp. *lactis* CCFM1018, and culturing was performed at 30-37° C. for at least 12 h to obtain a fermentation agent containing the *Lactococcus lactis* subsp. *lactis* CCFM1018.

Optionally, the bacterial cells in the fermentation solution were collected and mixed with a 3% sucrose solution to prepare a bacterial suspension.

Optionally, the bacterial suspension containing the *Lactococcus lactis* subsp. *lactis* CCFM1018 is mixed with a cytoprotective agent, and the mixture was freeze-dried at a low temperature to prepare a *Lactococcus lactis* subsp. *lactis* CCFM1018 freeze-dried preparation.

Example 8: Production of Milk Containing *Lactococcus lactis* Subsp. *Lactis* CCFM1018 Using Same Raw skimmed milk was sterilized with heat at 95° C. for 20 min, and then cooled to 4° C. Then the *Lactococcus lactis* subsp. *lactis* CCFM1018 fermentation agent was added, and the concentration reached $10^6$ CFU/ml or above. The milk product was stored under refrigeration at 4° C., and thus, milk containing live bacteria of the *Lactococcus lactis* subsp. *lactis* CCFM1018 of the disclosure was obtained.

Example 9: Preparation of Fermented Food Using *Lactococcus lactis* Subsp. *Lactis* CCFM1018 by Fermentation The *Lactococcus lactis* subsp. *lactis* CCFM1018 was used to prepare fermented dairy products, fermented bean products, or fermented fruit and vegetable products. The dairy products include milk, sour cream, and cheese; and the fruit and vegetable products include cucumber, carrot, beet, celery, and cabbage products. The *Lactococcus lactis* subsp. *lactis* CCFM1018 can be resistant to gastric acid and bile salts, promote excretion of a plasticizer and metabolites thereof from the body, reduce the content of the plasticizer and the metabolites thereof in serum, and significantly reduce the damage of the plasticizer and the metabolites thereof to testicular tissue and liver tissue.

The *Lactococcus lactis* subsp. *lactis* CCFM1018 of the disclosure has good resistance to gastric acid and bile salts, can promote excretion of the plasticizer DEHP and the metabolite MEHP thereof from the body, reduces the content of the plasticizer and the metabolite thereof in serum, and significantly reduces the damage of the plasticizer and the metabolite thereof to testicular tissue and liver tissue.

The *Lactococcus lactis* subsp. *lactis* CCFM1018 not only is significantly better than the intestinal resident bacteria *Escherichia coli* (DEHP: 5.86%, MEHP: 0.28%) and *Enterococcus faecalis* (DEHP: 1.75%, MEHP: 0.17%) in terms of in vitro adsorption of DEHP and MEHP (57.67% and 67.36% respectively), but also is better than the commercial strain *Lactobacillus rhamnosus* LGG (DEHP: 13.75%, MEHP: 15.60%). In rats, the *Lactococcus lactis* subsp. *lactis* CCFM1018 can significantly reduce the DEHP and MEHP content in serum (by 30.47% and 63.63% respectively compared to the blank control group), and at the same time increase the DEHP and MEHP content in feces (by 58.90% and 21.42% respectively compared to the blank control group). Therefore, the *Lactococcus lactis* subsp. *lactis* CCFM1018 of the disclosure can be used as an effective means to prevent and alleviate body damage caused by DEHP and MEHP, and does not have toxic or side effects of drugs. The *Lactococcus lactis* subsp. *lactis* CCFM1018 can be used to prepare pharmaceutical compositions and fermented food for alleviating and preventing the toxicity of DEHP and the metabolites thereof, and has a very broad application prospect.

Although the disclosure has been disclosed above in the preferred examples, it is not intended to limit the disclosure. Anyone skilled in the art can make various changes and modifications without departing from the spirit and scope of the disclosure. Therefore, the protection scope of the disclosure should be defined by the claims.

The invention claimed is:

1. A microbial composition, the composition comprising live *Lactococcus lactis* subsp. *lactis* CCFM1018 cells deposited on Feb. 11, 2018, at the Guangdong Microbial Culture Collection Center, Guangdong Institute of Microbiology, under the GDMCC number 60332, wherein:
   (a) the composition is a fermented food product prepared by fermentation of the *Lactococcus lactis* subsp. *lactis* CCFM1018 cells, wherein the fermented food product comprises dairy products, bean products, or fruit and vegetable products, wherein the dairy products comprise milk, sour cream, or cheese; and wherein the fruit and the vegetable products comprise cucumber, carrot, beet, celery, or cabbage, or
   (b) the composition is a microbial preparation in which the *Lactococcus lactis* subsp. *lactis* CCFM1018 cells are fermented, collected, mixed with a cytoprotective agent, and freeze-dried to obtain a freeze-dried preparation containing live cells of the *Lactococcus lactis* subsp. *lactis* CCFM1018.

2. The composition of claim 1, wherein the composition (a) is a liquid preparation.

3. The composition of claim 2, wherein the composition further comprises a sucrose solution.

4. A method of preparing a fermented product, the method comprising adding live *Lactococcus lactis* subsp. *lactis* CCFM1018 cells to fermentation raw materials to ferment for a period of time to obtain the fermented product.

5. The method of claim 4, wherein the fermented product is a food.

6. The method of claim 4, wherein the fermented product is a fermented beverage.

7. The method of claim 6, wherein the fermented beverage is a fermented dairy product prepared by inoculating milk with the live *Lactococcus lactis* subsp. *lactis* CCFM1018 cells and fermenting the milk at 30° C.-37° C. for at least 4 hours.

8. The method of claim 6, wherein the fermented beverage is a fermented fruit and vegetable product prepared by inoculating a fruit and a vegetable paste, ora fruit and a vegetable juice with the live *Lactococcus lactis* subsp. *lactis* CCFM1018 cells for fermentation.

* * * * *